(12) United States Patent  (10) Patent No.: US 8,303,567 B2
Stedman et al.  (45) Date of Patent: Nov. 6, 2012

(54) METHOD FOR DELIVERING A MACROMOLECULAR COMPLEX TO MUSCLE CELLS

(75) Inventors: Hansell H. Stedman, Norristown, PA (US); Charles R. Bridges, Villanova, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/008,379

(22) Filed: Jan. 18, 2011

(65) Prior Publication Data

US 2011/0112510 A1   May 12, 2011

Related U.S. Application Data

(63) Continuation of application No. 10/573,129, filed as application No. PCT/US2004/031322 on Sep. 24, 2004, now abandoned.

(60) Provisional application No. 60/506,367, filed on Sep. 26, 2003.

(51) Int. Cl.
*A61M 31/00* (2006.01)
(52) U.S. Cl. ...................................................... 604/511
(58) Field of Classification Search .................. 604/500, 604/507–509, 511
See application file for complete search history.

(56) References Cited

U.S. PATENT DOCUMENTS

| | | | |
|---|---|---|---|
| 5,069,662 A | 12/1991 | Bodden | |
| 5,320,605 A | 6/1994 | Sahota | |
| 5,451,207 A | 9/1995 | Yock | |
| 5,728,066 A | 3/1998 | Daneshvar | |
| 5,813,842 A | 9/1998 | Tamari | |
| 6,071,258 A | 6/2000 | Dalke et al. | |
| 6,177,403 B1 * | 1/2001 | Stedman | 514/1.2 |
| 6,267,747 B1 | 7/2001 | Samson et al. | |
| 6,508,777 B1 | 1/2003 | Macoviak et al. | |
| 6,537,241 B1 | 3/2003 | Odland | |
| 6,673,039 B1 | 1/2004 | Stedman et al. | |
| 6,699,231 B1 * | 3/2004 | Sterman et al. | 604/509 |
| 6,726,651 B1 | 4/2004 | Robinson et al. | |
| 6,776,771 B2 | 8/2004 | van Moorlegen et al. | |
| 7,214,369 B2 | 5/2007 | Wolff et al. | |
| 7,722,596 B2 | 5/2010 | Shapland et al. | |
| 2002/0107504 A1 | 8/2002 | Gordon | |
| 2003/0040665 A1 | 2/2003 | Khuri | |

(Continued)

FOREIGN PATENT DOCUMENTS

WO    WO 98/10088 A1    3/1998

(Continued)

OTHER PUBLICATIONS

Boshart, et al., A Very Strong Enhancer is Located Upstream of an Immediate Early Gene of Human Cytomegalovirus, Cell, 41:521-530 (Jun. 1985).

(Continued)

*Primary Examiner* — Kevin C Sirmons
*Assistant Examiner* — Bradley Osinski
(74) *Attorney, Agent, or Firm* — Howson & Howson LLP

(57) ABSTRACT

A method for transferring a macromolecular complex to muscle cells by exsanguinating a region of the subject's microvasculature and delivering the complex to this region under high hydrostatic pressure. A balloon catheter having a balloon that extends substantially the full length of the cannula that is inserted into the subject is provided for use in the systemic delivery of macromolecular complex.

4 Claims, 6 Drawing Sheets

U.S. PATENT DOCUMENTS

| | | |
|---|---|---|
| 2003/0216332 A1 | 11/2003 | Chamberlain et al. |
| 2004/0126879 A1 | 7/2004 | Schneider et al. |
| 2006/0116627 A1 | 6/2006 | Bridges et al. |
| 2006/0258980 A1 | 11/2006 | Bridges et al. |
| 2007/0073264 A1 | 3/2007 | Stedman et al. |
| 2009/0054823 A1 | 2/2009 | Bridges et al. |
| 2009/0287185 A1 | 11/2009 | Bridges |

FOREIGN PATENT DOCUMENTS

| | | |
|---|---|---|
| WO | WO 99/31982 A1 | 7/1999 |
| WO | WO 99/43360 A1 | 9/1999 |
| WO | WO 99/59666 A1 | 11/1999 |
| WO | WO 2005/027995 A3 | 3/2005 |
| WO | WO 2005/030292 A2 | 4/2005 |
| WO | WO 2006/039218 A2 | 4/2006 |

OTHER PUBLICATIONS

Bridges, et al., Global Cardiac-Specific Transgene Expression Using Cardiopulmonary Bypass with Cardiac Isolation, Ann. Thorac. Surg., 73:1939-1946 (Feb. 2002).

Gossen, et al., Transcriptional Activation by Tetracyclines in Mammalian Cells, Science, 268(5218):1766-1769 (Jun. 23, 1995).

Greelish, et al., Stable Restoration of the Sarcoglycan Complex in Dystrophic Muscle Perfused with Histamine and a Recombinant Adeno-Associated Viral Vector, Nature Medicine, 5(4):439-443 (Apr. 1999).

Harvey, et al., Inducible Control of Gene Expression: Prospects for Gene Therapy, Curr. Opin. Chem. Biol., 2:512-518 (Aug. 1998).

Koenig, et al., The Complete Sequence of Dystrophin Predicts a Rod-Shaped Cytoskeletal Protein, Cell, 53:219-228 (Apr. 22, 1988).

Li, et al., Synthetic Muscle Promoters: Activities Exceeding Naturally Occurring Regulatory Sequences, Nature Biotechnology, 17:241-245 (Mar. 1999).

Magari, et al., Pharmacologic Control of a Humanized Gene Therapy System Implanted into Nude Mice, J. Clin. Invest., 100(11):2865-2872 (Dec. 1997).

No, et al., Ecdysone-Inducible Gene Expression in Mammalian Cells and Transgenic Mice, Proc. Natl. Acad. Sci., 93:3346-3351 (Apr. 1996).

Ragot, et al., Efficient Adenovirus-Mediated Transfer of a Human Minidystrophin Gene to Skeletal Muscle of mdx Mice, Nature, 361:647-650 (Feb. 18, 1993).

Sambrook, et al., Functional Components of Mammalian Expression Vectors, Molecular Cloning, 16.5-16.6 (1989).

Stokes, et al., Experimental Maintenance of Life by a Mechanical Heart and Lung During Occlusion of the Venae Cavae Followed by Survival, Surgery, Gynecology and Obstetrics, 91: 138-156 (1950).

Wang, et al., Ligand-Inducible and Liver-Specific Target Gene Expression in Transgenic Mice, Nature Biotechnology, 15:239-243 (Mar. 1997).

Wang, et al., Positive and Negative Regulation of Gene Expression in Eukaryotic Cells with an Inducible Transcriptional Regulator, Gene Therapy, 4:432-441 (May 1997).

Yue, et al., Microdystrophin Gene Therapy of Cardiomyopathy Restores Dystrophin-Glycoprotein Complex and Improves Sarcolemma Integrity in the Mdx Mouse Heart, Circulation, 108:1-7 (Sep. 30, 2003).

Jul. 30, 2008 Office Action and Notice of References Cited in priority U.S. Appl. No. 10/573,129.

Response to Jul. 30, 2008 Office Action in priority U.S. Appl. No. 10/573,129.

Apr. 7, 2009 Office Action and Notice of References Cited in priority U.S. Appl. No. 10/573,129.

Response to Apr. 7, 2009 Office Action in priority U.S. Appl. No. 10/573,129.

Jan. 8, 2010 Office Action in priority U.S. Appl. No. 10/573,129.

Response to Jan. 8, 2010 Office Action in priority U.S. Appl. No. 10/573,129.

Aug. 31, 2010 Office Action in priority U.S. Appl. No. 10/573,129.

International Search Report and Written Opinion in priority International Patent Application No. PCT/US04/31322.

Aug. 16, 2010 Office Action in U.S. Appl. No. 11/664,245.

Response to Aug. 16, 2010 Office Action in U.S. Appl. No. 11/664,245.

Feb. 24, 2011 Office Action in U.S. Appl. No. 11/664,245.

Nov. 19, 2010 Office Action in U.S. Appl. No. 12/086,024.

Response to Nov. 19, 2010 Office Action in U.S. Appl. No. 12/086,024.

Response to Feb. 24, 2011 Office Action in U.S. Appl. No. 11/664,245.

Aug. 11, 2011 Office Action in U.S. Appl. No. 11/664,245.

Apr. 27, 2011 Office Action in U.S. Appl. No. 12/086,024.

Response to Apr. 27, 2011 Office Action in U.S. Appl. No. 12/086,024.

Notice of Allowance, Notice of Allowability, and Reasons for Allowance in U.S. Appl. No. 12/086,024.

* cited by examiner

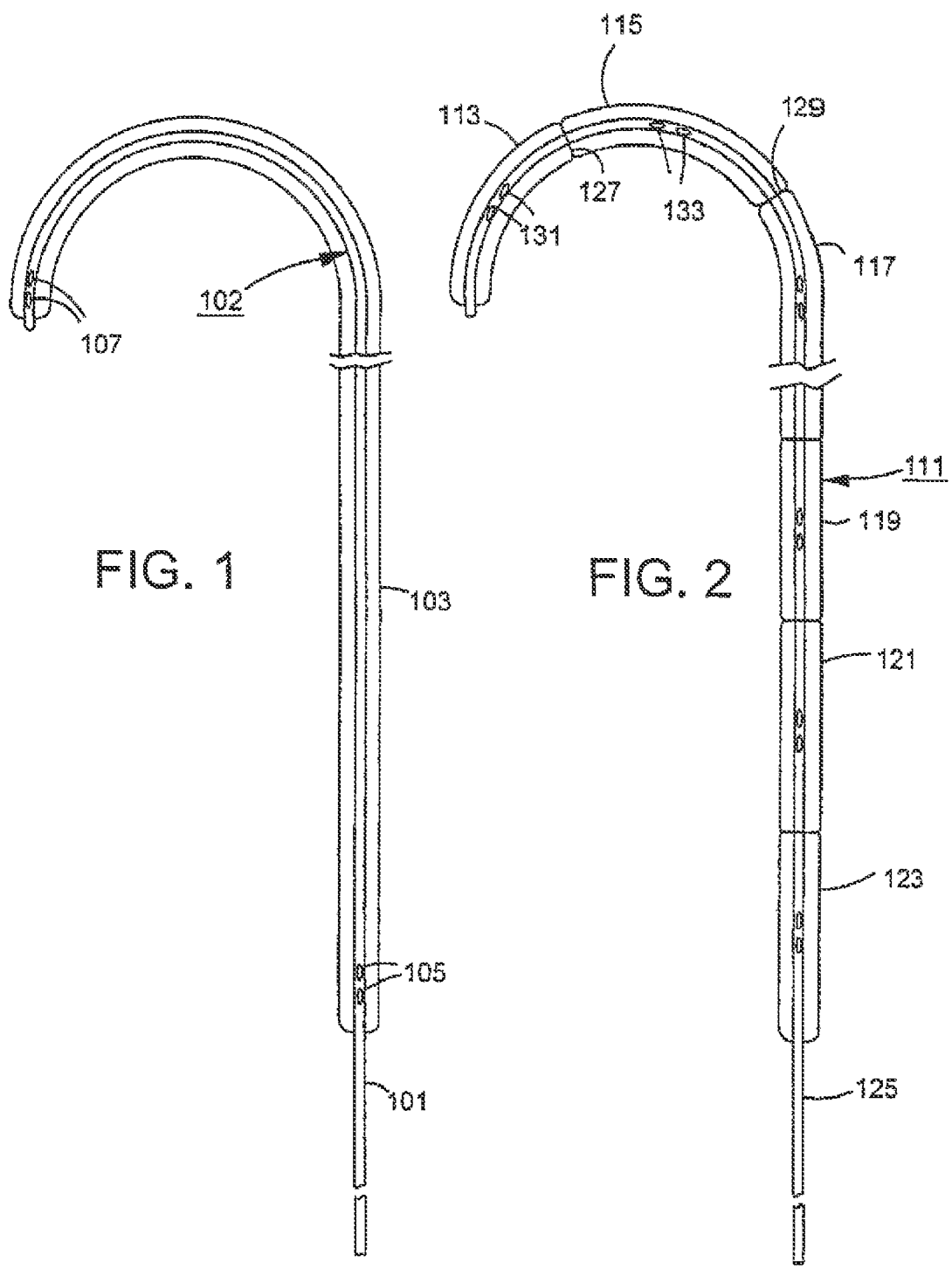

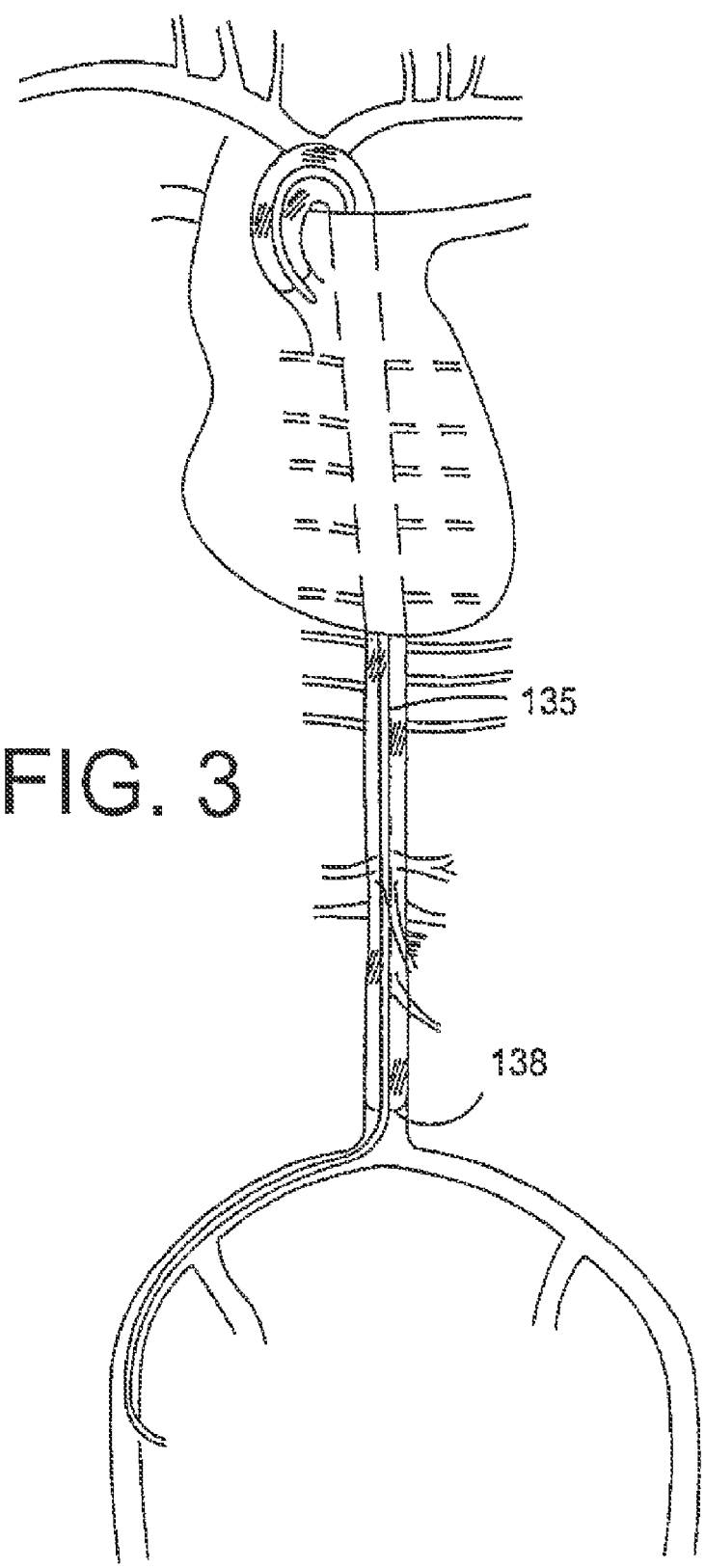

METHOD FOR DELIVERING A MACROMOLECULAR COMPLEX TO MUSCLE CELLS

CROSS-REFERENCE TO RELATED APPLICATIONS

This application is a continuation of U.S. patent application Ser. No. 10/573,129, filed Mar. 23, 2006, now abandoned, which is a national stage application under 35 USC 371 of PCT/US04/31322, filed Sep. 24, 2004, which claims the benefit under 35 USC 119(e) of U.S. Patent Application No. 60/506,367, filed Sep. 26, 2003 (now expired), all of which are incorporated by reference herein.

BACKGROUND OF THE INVENTION

The invention relates generally to the field of gene therapy.

A variety of methods have been described in the literature as being useful for delivering a desired molecule into a target cell. The combined use of 1) complete vascular isolation using tourniquets and proximal arterio-venous cannulation, 2) systemic heparinization to prevent thrombosis, 3) peripheral vasodilation to optimize perfusion of muscle capillaries, and 4) histamine to produce physical gaps between adjacent endothelial cells has achieved widespread, homogeneous, vector-independent gene transfer to muscles of entire extremities. These studies began with marker genes and were then applied to several disease models in larger rodents and dogs. However, the four essential components of the protocol listed above have stymied clinical translation because of the inherent risk of hemorrhage, hypotension, and pulmonary dysfunction.

For example, U.S. Pat. No. 6,177,403 describes a kit for delivering a macromolecular assembly to the extravascular tissue of an animal. This kit involves the use of a vascular permeability-enhancing agent and a vasodilating agent. However, such agents can be associated with undesirable side effects, including short-term toxicity, which minimizes the usefulness of such methods.

Systems for pressure mediated selective delivery of therapeutic substances to specific areas of organs and cannula useful therein have been described. See, e.g., WO 99/59666, Nov. 25, 1999. However, these methods and devices avoid systemic delivery of therapeutic substances.

Further, studies in large animal models have revealed a trade-off between the efficiency of gene transfer using known methods and the inherent safety of the required pharmacological interventions.

What are needed are methods that facilitate delivery of target molecules to the desired host cell while minimizing side effects.

SUMMARY OF THE INVENTION

The present invention provides a method of transferring a macromolecular complex from the vascular space to the interstitium in a subject in the absence of permeability enhancing agents by isolating a region of the subject's microvasculature and partially or completely exsanguinating that region. Thereafter, the complex is delivered to the exsanguinated region under rapidly applied high hydrostatic pressure. Also provided is a balloon catheter for systemic delivery of the macromolecular complex of the invention and kits useful for performing the method of the invention.

The present invention provides the first protocol for somatic gene transfer to muscle that achieves scale-independent, limb-wide transduction of nearly 100% of fibers, while avoiding the risks of histamine, papaverine, heparin, and arterial access.

Other aspects and advantages of the present invention will be readily apparent from the following detailed description of the invention.

BRIEF DESCRIPTION OF THE DRAWINGS

FIG. 1 is a schematic side elevational view of an internally occlusive aortic balloon catheter according to the present invention with a cannula shaft configured for retrograde deployment via femoral artery access;

FIG. 2 is a schematic side elevational view of an internally occlusive aortic balloon catheter according to the present invention with a cannula shaft configured for retrograde deployment via femoral artery access, and showing compartments in the balloon, each compartment containing separate fluid ports;

FIG. 3 is a schematic anterior view of a patient, illustrating placement of the aortic balloon catheter of FIG. 1;

DETAILED DESCRIPTION OF THE INVENTION

Figure 4:
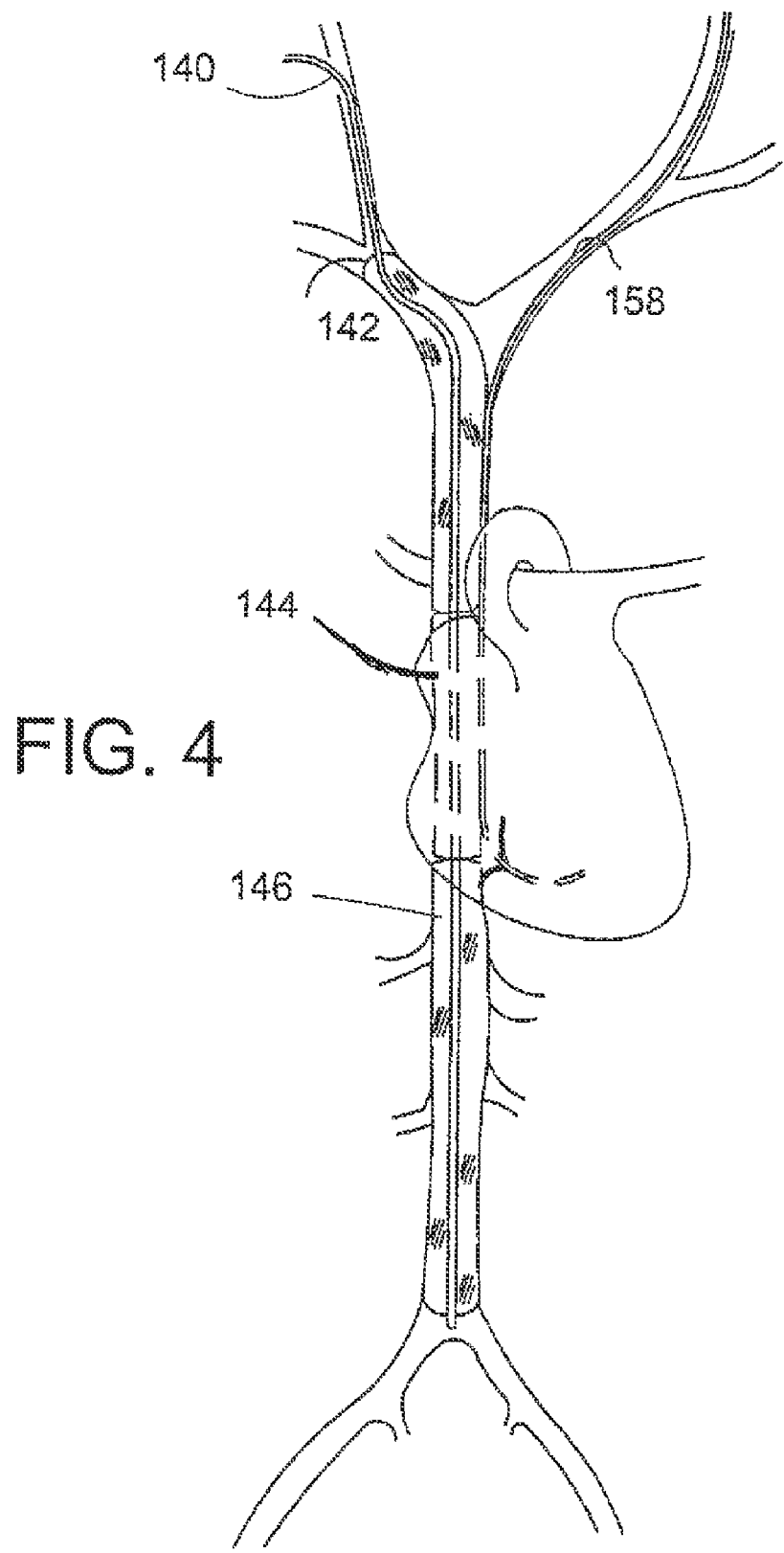
FIG. 4 is a schematic anterior view of a patient, illustrating placement of a segmented balloon catheter in the vena cavae.

The inventors provide a method by which rapid, mechanical distention of the venular endothelium by afferent infusion from a distal site safely facilitates macromolecular transport from the vascular space to the muscle interstitium (e.g., skeletal muscle). Pressurized infusion through a large-bore catheter in a distal, superficial vein according to the invention results in uniform, scale- and vector-independent transduction of myofibers in anatomic domains isolated from the central circulation by tourniquet. This approach is rapid, minimally invasive, and avoids pharmacological interference with cardiovascular homeostasis. Accordingly, the present invention provides uniform gene transfer to the muscle fibers of an entire extremity in a mammal larger than a rodent, which is applicable to large mammals, including humans.

In one aspect, the invention provides a method of transferring a heterologous macromolecular complex from the vascular space to the interstitium surrounding muscle cells in a subject in the absence of permeability enhancing agents by delivering the complex to a subject's microvasculature under high hydrostatic pressure. When performed systemically, this method is performed with the patient under total circulatory arrest and under hypothermic conditions.

Exsanguination followed by high pressure delivery of a heterologous molecule to the interstitial space between the epithelial cells of the microvasculature and into surrounding muscle cells facilitates entry of the molecule into the interstitial space. Further, subjecting the patient to hypothermia, according to one aspect of the invention involving isolation of the central and peripheral circulation, enhances safe entry of the molecule.

Without wishing to be bound by the mechanism of the invention, the inventors theorize that the reasons for the success of the method of the invention in obtaining efficient delivery of macromolecules to larger animals are based upon differences in the anatomy of mice, which are typically used in initial gene therapy studies and larger animals, including humans. More particularly, the inventors have noted that the veins of larger mammals, including humans contain one-way valves in large veins and in vessels down to as small as about 1 mm; whereas these peripheral valves do not exist in mice. The inventors theorize that the presence of these valves contributes to preventing efficient gene transfer in larger animals. Additionally, the inventors have noted that the basal laminate of the vessels becomes progressively thicker in larger animals as from the top of the animal (e.g., head, neck) to the bottom of the animal as these vessels are subject to a higher pressure gradient. This thickening of the basal laminate is not present in mice, which have even been observed to have a "leaky" vasculature. In view of this theory, the inventors have termed the method of the invention ATVRx, Afferent TransVenular Retrograde eXtravasation. These anatomical differences between a small mammal such as the mouse and larger mammals were not previously recognized as significant with respect to delivery of macromolecules to muscle cells prior to the present invention.

The term "heterologous" includes, among other things, molecules that are not natively found in combination with the material with which they are being associated. For example, a heterologous molecule is not found in a target cell in the form in which it is delivered to the cell. As another example, heterologous refers to molecules, including nucleic acid sequences, which are derived from the same source but are natively non-contiguous, or molecules that are derived from different sources. This definition is not a limitation on the present invention.

The method of the invention is well suited for avoiding an immune response, and particularly, a response from circulating antibodies. The method of the invention is performed following isolation and at least partial resanguination of a region of the vasculature, followed by delivery of the macromolecular complex. The absence of circulating blood in the area to which the macromolecular complex is infused minimizes the risk of inducing an immune response and clearance of the macromolecular complex by neutralizing antibodies. Thus, in one embodiment, the method of the invention permits administration, or readministration, of a macromolecular complex to which the patient has preexisting circulating antibodies. In some embodiments, resanguination of the targeted portion of the microvasculature follows flushing of residual macromolecular complex (i.e., macromolecular complex not taken up by the extravascular tissue, e.g., muscle cells) from the area following infusion. This flushing step can be performed by washing the area with saline solution that contains no complex. Thus, the method of the invention minimizes the exposure of the subject to the complex, thereby reducing the risk of an immune reaction. Further, the method of the invention minimizes, or eliminates, exposure of other non-targeted areas of the body to the complex. For example, when the area targeted is a limb, isolation of the limb minimizes or completely eliminates exposure of the liver or lung to the complex.

Advantageously, the method of the invention also avoids unwanted elements of the blood, e.g., cells, platelets, and tissue-reactive plasma components, from contacting the macromolecular complex. Thus, the method of the invention also avoids activation of various clotting factors and other factors that could interfere with the transfer of the macromolecular complex.

The invention further provides compositions and devices useful for performing this method, as well as other functions that will be apparent to those of skill in the art given the guidance provided in this application.

As used herein, the term muscle cells include both skeletal muscle cells and smooth muscle cells. In one embodiment, the muscle cells are cardiac muscle. However, other muscle cells can readily be targeted.

As used herein, the term "high hydrostatic pressure" generally refers to a pressure in the range of 50 mm Hg to 500 mm Hg. Suitable pressures within this range, e.g., 75 mm Hg, 100 mm Hg, 150 mm Hg, 200 mm Hg, 250 mm Hg, 300 mm Hg, 350 mm Hg, 400 mm Hg, or 450 mm Hg, or others within or outside this range may be readily selected. Some of the values provided herein are measured in torr, which at 0° C. is equivalent to mm Hg. High hydrostatic pressure is applied according to the invention by a low resistance (large bore) catheter or cannula in either a vein or artery, or by other methods that will be readily apparent to one of skill in the art.

Typically, the high hydrostatic pressure described herein is rapidly applied by way of at least one low resistance catheter or cannula in either a vein or an artery. Currently, in a preferred embodiment, the catheter or cannula is applied in a vein.

I. Macromolecular Complex

As used herein, the term "macromolecular complex" encompasses any biologically useful moiety that can be transferred into targeted cells (e.g., muscle cells). Examples of suitable macromolecular complexes include vectors composed of nucleic acids, including RNA and DNA molecules, dominant negative mutants, an enzyme, a protein, peptide, or non-proteinaceous molecule, which may include small molecules or other chemical moieties.

Desirable RNA molecules include tRNA, dsRNA, ribosomal RNA, catalytic RNAs, siRNA, small hairpin RNA, trans-splicing RNA, and antisense RNAs. These RNA molecules can be delivered in the form of a transgene carried by a vector or by other suitable means.

The macromolecular complexes of the invention are not limited by size, but rather encompass molecules that, due to their large size, are not able to enter the cell on their own as well as molecules that can infect or transfect cells without the application of the present method.

A. Vectors

A vector includes plasmids, episomes, cosmids, viral vectors, phage, "naked DNA", any of which desirably contains a transgene under the control of regulatory sequences that direct expression thereof in a target cell.

The transgene is a nucleic acid sequence, heterologous to the vector sequences flanking the transgene, which encodes a polypeptide, protein, or other product, of interest. The nucleic acid coding sequence is operatively linked to regulatory components in a manner that permits transgene transcription, translation, and/or expression in a host cell. Suitably, these transgenes may also carry a desired RNA molecule, as described herein.

In one embodiment, the macromolecular complex comprises a viral vector. Examples of suitable viral vectors include, without limitation, adenoviruses, picornavirus, adeno-associated viruses, retroviruses, baculoviruses, and lentiviruses, among others. For example, a macromolecular complex can be an adenoviral vector comprising a human minidystrophin gene [Ragot et al, 1993, Nature 361:647-650)

or pAdDeltaRSV, which is a modified plasmid containing a full-length dystrophin cDNA [Koening et al, 1998, Cell 53:219-228] with a backbone of a pBSA-2 vector with an RSV promoter operably linked to the dystrophin cDNA, and containing adenoviral 5' and 3' ITRs flanking the promoter-dystrophin cDNA. Currently, adeno-associated viruses (AAV) are considered particularly well suited for delivery to muscle. Typically, a recombinant AAV is composed of, at a minimum, a transgene and its regulatory sequences, and 5' and 3' AAV inverted terminal repeats (ITRs), all packaged in a capsid composed at least in part of proteins encoded by an AAV "cap" gene. In one desirable embodiment, the ITRs of AAV serotype 2 are used. However, ITRs from other suitable serotypes may be selected. However, the invention is not limited to use of viral vectors or, when viral vectors are selected, to use of rAAV.

B. Transgene

When present in a macromolecular complex as defined herein, a transgene is selected with regard to the biological effect desired.

One example of a useful RNA sequence is a sequence which inhibits or extinguishes expression of a targeted nucleic acid sequence in the treated animal. Typically, suitable target sequences include oncologic targets and viral diseases. See, for examples of such targets, the oncologic targets and viruses identified below in the section relating to immunogens.

Another example is for treatment of the symptoms associated with a muscular disorder or cardiomyopathy, one may select from among a number of transgenes associated with muscular dystrophies and/or cardiomyopathies. Examples of suitable genes include, a sarcoglycan protein (e.g., $\alpha$, $\beta$, or $\delta$, or $\gamma$), a Muscular Dystrophy protein (dystrophin or utrophin), a minidystrophin or microdystrophin protein [See, e.g., Y. Yue, et al, Circulation, 108:1623 (September 2003), e-publ. Sep. 2, 2003], calpain, a congenital/limb Girdle Muscular Dystrophy protein (Fukutin, Fukutin-related protein, telethonin, or laminin). Other suitable genes may include beta adrenergic receptor kinase 1 (bARK1) and inhibitors of binding between cardiac myocyte adrenergic receptors and a protein of the Gq subclass. Still other genes include, e.g., carnitine palmityl transferase (CPT) 1 and CTP2, which is implicated in CPT deficiency; dysferlin, which is implicated in limb-girdle MD type 2B and Miyoshi myopathy; thymidine phosphorylase; SMN2 (SMNC), which is implicated in spinal muscular atrophy; and insulin-like growth factor (e.g., Igfl), among others. Still other genes include SERCA and phospholambin, which are implicated in cardiomyopathies.

In another embodiment, a transgene may be selected from among transgenes for which expression from a target cell is desired. Such products include those used for treatment of hemophilia, including hemophilia B (including Factor IX) and hemophilia A (including Factor VIII and its variants, such as the light chain and heavy chain of the heterodimer and the B-deleted domain; U.S. Pat. No. 6,200,560 and U.S. Pat. No. 6,221,349).

For example, the Factor VIII gene codes for 2351 amino acids and the protein has six domains, designated from the amino to the terminal carboxy terminus as A1-A2-B-A3-C1-C2 [Wood et al, Nature, 312:330 (1984); Vehar et al., Nature 312:337 (1984); and Toole et al, Nature, 342:337 (1984)]. Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, which releases the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

In some embodiments, the minigene comprises first 57 base pairs of the Factor VIII heavy chain that encodes the 10 amino acid signal sequence, as well as the human growth hormone (hGH) polyadenylation sequence. In alternative embodiments, the minigene further comprises the A1 and A2 domains, as well as 5 amino acids from the N-terminus of the B domain, and/or 85 amino acids of the C-terminus of the B domain, as well as the A3, C1 and C2 domains. In yet other embodiments, the nucleic acids encoding Factor VIII heavy chain and light chain are provided in a single minigene separated by 42 nucleic acids coding for 14 amino acids of the B domain [U.S. Pat. No. 6,200,560].

As used herein, a therapeutically effective amount is an amount of macromolecular complex (e.g. a rAAV) that produces sufficient amounts of Factor VIII to decrease the time it takes for a subject's blood to clot. Generally, severe hemophiliacs having less than 1% of normal levels of Factor VIII have a whole blood clotting time of greater than 60 minutes as compared to approximately 10 minutes for non-hemophiliacs.

The present invention is not limited to any specific Factor VIII sequence. Many natural and recombinant forms of Factor VIII have been isolated and generated. Examples of naturally occurring and recombinant forms of Factor VIII can be found in the patent and scientific literature including, U.S. Pat. No. 5,563,045, U.S. Pat. No. 5,451,521, U.S. Pat. No. 5,422,260, U.S. Pat. No. 5,004,803, U.S. Pat. No. 4,757,006, U.S. Pat. No. 5,661,008, U.S. Pat. No. 5,789,203, U.S. Pat. No. 5,681,746, U.S. Pat. No. 5,595,886, U.S. Pat. No. 5,045,455, U.S. Pat. No. 5,668,108, U.S. Pat. No. 5,633,150, U.S. Pat. No. 5,693,499, U.S. Pat. No. 5,587,310, U.S. Pat. No. 5,171,844, U.S. Pat. No. 5,149,637, U.S. Pat. No. 5,112,950, U.S. Pat. No. 4,886,876, WO 94/11503, WO 87/07144, WO 92/16557, WO 91/09122, WO 97/03195, WO 96/21035, WO 91/07490, EP 0 672 138, EP 0 270 618, EP 0 182 448, EP 0 162 067, EP 0 786 474, EP 0 533 862, EP 0 506 757, EP 0 874 057, EP 0 795 021, EP 0 670 332, EP 0 500 734, EP 0 232 112, EP 0 160 457, Sanberg et al., XXth Int. Congress of the World Fed. Of Hemophilia (1992), and Lind et al., *Eur. J. Biochem.*, 232:19 (1995).

Nucleic acids sequences coding for the above-described Factor VIII can be obtained using recombinant methods or by deriving the sequence from a vector known to include the same. Furthermore, the desired sequence can be isolated directly from cells and tissues containing the same, using standard techniques, such as phenol extraction and PCR of cDNA or genomic DNA [See, e.g., Sambrook et al]. Nucleotide sequences can also be produced synthetically, rather than cloned. The complete sequence can be assembled from overlapping oligonucleotides prepared by standard methods and assembled into a complete coding sequence [See, e.g., Edge, *Nature* 292:757 (1981); Nambari et al, *Science,* 223: 1299 (1984); and Jay et al, *J. Biol. Chem.* 259:6311 (1984).

Furthermore, the invention is not limited to human Factor VIII. Indeed, it is intended that the present invention encompass Factor VIII from animals other than humans, including but not limited to, companion animals (e.g., canine, felines, and equines), livestock (e.g., bovines, caprines and ovines), laboratory animals, marine mammals, large cats, etc.

The complexes may contain a nucleic acid coding for fragments of Factor VIII that is itself not biologically active, yet when administered into the subject improves or restores the blood clotting time. For example, as discussed above, the Factor VIII protein comprises two polypeptide chains: a heavy chain and a light chain separated by a B-domain that is cleaved during processing. As demonstrated by the present invention, co-tranducing recipient cells with the Factor VIII heavy and light chains leads to the expression of biologically active Factor VIII. Because, however, most hemophiliacs contain a mutation or deletion in only one of the chain (e.g., heavy or light chain), it may be possible to administer only the chain defective in the patient to supply the other chain.

Examples of other transgene products include myostatin inhibitors, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other suitable proteins as for delivery by the method of the invention will be readily apparent. Similarly, transgenes encoding proteins that are expressed on the cell surface of the targeted cells can be delivered by the method of the invention.

C. Regulatory Sequences and Construction of Macromolecular Complexes

Suitably, macromolecular complexes carrying transgenes further contain regulatory sequences operably linked to the encoded gene product. In addition to the major elements identified above, the macromolecular complex (e.g., a vector) also includes conventional control elements that are operably linked to the transgene in a manner that permits its transcription, translation and/or expression in a cell transfected with the macromolecular complex.

As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters that are native, constitutive, inducible and/or tissue-specific, are known in the art and may be utilized.

In one embodiment, the regulatory sequences are optimized for expression in the muscle and/or comprise tissue-specific promoters. For instance, if expression in skeletal muscle is desired, a promoter active in muscle can be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). However, one of skill in the art can readily select a suitable constitutive, inducible, or regulated promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science,* 268:1766-1769 (1995), see also Harvey et al, *Curr. Opin. Chem. Biol.,* 2:512-518 (1998)], the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. Other types of inducible promoters that may be useful in this context are those that are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Methods for assembling and producing a variety of different macromolecular complexes as defined herein are known to those of skill in the art and have been described in textbooks and in the literature. See, e.g., Sambrook et al, Molecular cloning: A Laboratory Manual, Cold Spring Harbor Press, Cold Spring Harbor, N.Y. (1989). Selection and production of the macromolecular complex is not a limitation of the present invention.

II. Transferring a Macromolecular Complex to a Limb of a Subject.

In one embodiment, the method of the invention is used to deliver a macromolecular complex to an arm or a leg of a subject. In order to effectively deliver the complex according to the invention, the vasculature of the limb is isolated.

The limb is exsanguinated and sufficient pressure is applied to isolate the limb. In one embodiment, a limb is isolated by applying pressure at a girdle between the limb and the trunk of the subject's body. Typically, this is accomplished by inflating a tourniquet at the pelvic ring in order to isolate a leg and/or inflating a tourniquet at the shoulder girdle in order to isolate an arm and fluid is removed through use of an elastic band (e.g., an Esmark wrap) that is applied in spiral fashion starting at the foot or hand and wrapping proximally under force. In another embodiment, two or more of the subject's limbs can be isolated simultaneously. For example, pressure can be applied in order to simultaneously isolate both legs from the upper portion of the body. Typically, this is accomplished by use of a tourniquet that is placed around the trunk infrarenally. In still another embodiment, an arm and a leg are isolated at the same time, using the techniques described herein. Methods of applying pressure to isolate the circulation of a limb or limbs are known to those of skill in the art and are not a limitation on the present invention.

Once the desired limb and/or limbs are isolated and exsanguinated, the macromolecular complex is infused into each limb at a high hydrostatic pressure. It is anticipated that efficiency of gene transfer to a limb will increase as the pressure increases through the range provided herein. For example, in a small mammal, efficiency of gene transfer has been demonstrated to increase as the pressure increases through the range 100, 200, and 400 torr.

Exsanguination and infusion can be readily accomplished using a suitable, commercially available, balloon catheter located in a suitable vessel of the limb (e.g., a vein or artery). In one embodiment, it is desirable to utilize a balloon tip catheter placed percutaneously using a dilator to maximize the bore available. Optionally, it may be desirable to have a second inflatable tourniquet placed just proximal to the catheter insertion site, distal to inflated balloon tip to minimize leak around catheter at wall of vein. In another embodiment, it is desirable to utilize a larger bore non-balloon tip catheter placed through a very small cut down (1.5 cm incision).

Typically, the macromolecular complex is infused in a physiologically compatible solution. In one embodiment, the solution contains physiologic solution that may be readily selected from among saline, isotonic dextrose, or a glycerol solution, among others that will be apparent to one of skill in the art given the information provided herein. In one embodiment, the physiologic solution is oxygenated in order to maximize the safety margin and minimize the risk of limb ischemia. However, the invention is not so limited. Suitably, the total volume of the solution infused into the limb is in the range of 20 to 100%, 25 to 90%, 30 to 80%, 40 to 70%, 50 to 60%, of the estimated volume of the extremity. The concentration of the macromolecular complex in the solution can vary depending upon the type of complex selected. However, given the information provided in the present invention, one of skill in the art can readily select higher or lower volumes.

The limb is resanguinated in a conventional manner, e.g., by lowering the pressure in the proximal tourniquet.

III. A Method of Transferring a Macromolecular Complex Systemically

In one embodiment, the present invention permits the transfer of a macromolecular complex as defined herein to extravascular tissue systemically. In one particularly desirable embodiment, systemic delivery involves separating the central circulation, i.e., all vessels directly supplying the thoracic and abdominal viscera, from the peripheral circulation, i.e., vessels supplying the skeletal muscles. The method involves restricting the flow of fluids through the central circulation using the balloon catheter of the invention. Thus, the method is particularly well suited for targeted delivery of a heterologous molecule to muscle cells of a subject, while avoiding delivery to the organs. This is particularly advantageous where delivery to a selected organ, e.g., the liver or lung, is undesirable in view of the selected transgene, the selected vector, or some other component of a heterologous molecule.

According to the present invention, a patient is placed under total circulatory arrest. Typically, this is performed as follows. The patient is placed under general endotracheal anesthesia, heparin is administered and total circulatory arrest is achieved by way of a carotid-jugular or femoral cannulation using a pump oxygenator. Known techniques are used to accomplish the placement of these conventional cannulae in suitable vessels, e.g., in the carotid artery and/or in a femoral artery. Conventional heart-lung cannulae are utilized.

For example, one catheter may be threaded from a femoral position (e.g., a femoral artery) and through the aorta. Alternatively, the catheter may be threaded from the carotid artery in a superior-to-inferior direction through the aorta. A second catheter may be threaded into the vena cava in either a superior-to-inferior director or in an inferior-to-superior to direction. When the catheter is inserted in the superior-to-inferior direction, it is preferably inserted into a human subject through the right jugular vein or through another vein which communicates with the superior vena cava. When the catheter is inserted in the inferior-to-superior direction, it is preferably inserted into a human subject through a femoral vein of the subject, another it may be inserted through a vein that communicates with the inferior vena cava. Alternatively, the catheter may be threaded entirely through the subject (e.g., extending from both the subject's femoral vein and the subject's jugular vein).

The patient is rendered hypothermic, in the range of 15 to 18° C. using the protocols described previously for pediatric cardiac surgery and adult aortic arch reconstruction. See, e.g., U.S. Pat. No. 6,492,103, "System for organ and tissue preservation and hypothermic blood substitution". The patient is then partially exsanguinated and decannulated from the first and second heart-lung cannulae.

One balloon catheter of the invention is inserted into one of the cannulation sites and threaded so that upon inflation, the balloon occludes both the superior vena cava and inferior venae cava. Another balloon catheter of the invention is inserted into the other cannulation site and threaded through the aorta to a position just adjacent to the aortic arch. Desirably, this internal occlusion balloon runs from the aortic bifurcation to the aortic arch. Proper positioning of these catheters may involve fluoroscopy or ultrasound techniques such as are known to those of skill in the art. Once positioned properly, the balloon catheters are inflated so that one balloon catheter occludes the venae cavae and the second balloon catheter occludes the aortic space.

Typically, the catheters are inflated to a pressure exceeding that applied from cannulae in the extremities of the patient. In one embodiment, the macromolecular complex is delivered in a physiologic solution as described above. In one embodiment, the solution is oxygenated. In one embodiment, the solution is an oxygenated, physiologic saline. Suitably, the complex in solution is then infused to all four of the patient's extremities via the cannulae located therein.

The solution can be infused under high pressure, as defined herein. Alternatively, the pressure in the microvascular space can be reduced below physiological levels by the catheters and the exsanguination procedure. Thereafter, as pressure/volume are increased toward baseline pressure/volume via delivery from the cannulae at the extremities, delivery to extravascular tissue will increase. Typically, about 0.5 to 4 liters of liquid are delivered according to this method. However, smaller or larger amounts can be readily used. For example, in a 70 kg adult, about 1.5 to 2 liters are suitable for an isolated limb and 3 to 4 liters should be well tolerated systemically. In a small child, about 0.5 liters to 1 liter can be used in an isolated limb and 1 to 2 liters can be used systemically. However, these amounts can be readily adjusted by one of skill in the art, taking into consideration the information provided herein and that which is known to one of skill in the art.

Following dissipation of the initial pressure gradient, typically about 2 minutes, in one embodiment, the solution is allowed to dwell. Typically, the fluid is permitted to dwell for about 30 seconds to 30 minutes, taking into consideration such factors as whether this dwell period is being utilized during system delivery or delivery to a limb as described above. For example, a suitable dwell period for system delivery may be from about 30 second to 1 minute, to about 90 seconds, or longer. However, longer dwell periods may be suitable for delivery to the limb, e.g., from about 1 minute to about 20 minutes, or longer. However, longer or shorter dwell periods may be readily selected given the information provided herein.

Optionally, the solution is flushed prior to withdrawing the balloon catheters and reinsertion of the heart-lung cannulae. The heart-lung cannulae are then reinserted and the patient is then resanguinated and rewarmed until hemodynamically stable. The cannulae are removed and the vessels repaired under direct vision. After closure of the small incision, the patient is extubated after weaning parameters are met. In the post procedural period, there is an anticipated need for oxygen support and hemodynamic monitoring as residual fluid in the interstitium is progressively mobilized and excreted by way of the kidneys. For large volume loads, hemofiltration may be required. Optionally, hemofiltration can be instituted in the operating room before decannulation. The method of the invention may involve subjecting the animal to extracorporeal circulatory support and oxygenation. Preferably, a heart-lung machine is used according to methods known in the art. Extracorporeal circulatory support and oxygenation permits blood flow to the lungs of the animal to be minimized, thus minimizing exudation from the pulmonary blood vessels of the animal into the lungs.

A method of subjecting a human to extracorporeal circulatory support and oxygenation has been described in U.S. Pat. No. 6,177,403. For example, an extracorporeal lung support (ECLS) pump oxygenator can be connected to a pair of cannulae inserted into the human, where one cannula extends into the right atrium of the human, and the other cannula extends into the aorta of the human. Blood is withdrawn from the right atrium, oxygenated extracorporeally, and returned to the atrium of the human at a controlled pressure and flow rate. Using this method, blood flow to the lungs is minimized, and exudation from pulmonary blood vessels into the parenchyma of the lungs is minimized Hepatic blood flow in the human may also be occluded.

Because an oxygen-transporting agent is provided to the vessel, the vessel can remain occluded, and the vector and agents can remain within the vessel for an extended period. In those embodiments in which a clearance solution is provided to the vessel, excess vector and agents are removed from the vessel prior to re-establishing systemic blood circulation in the animal, thereby minimizing any potential undesirable effects caused by the presence of the vector or agents in an area of the animal's body other than the vessel.

Whole blood, temporarily retained the venous reservoir of a modified (enlarged venous reservoir) pump-oxygenator, is reinfused to the patient via the oxygenator and the arterial cannula, while saline is removed from the venous cannula and cycled through a red blood cell recovery device (such as the commercially available "Cell Saver" device). This process is continued until the patient's entire blood volume is restored from the venous reservoir. After this point, the entire erythrocyte mass of the recovered saline perfusate is spun down and reinfused as appropriate, during a process of ongoing hemoconcentration by hemofiltration. Once the hematocrit is estimated to be above approximately 15%, warming begins by way of the oxygenator and continues until the patient reaches 37° C.

Although the method of the invention is particularly well suited for delivery of heterologous macromolecular complexes to target cells without utilizing vascular permeability-enhancing agents, one of skill in the art may utilize the devices and methods of the present invention in combination with such agents. Such agents include, e.g., histamine, acetylcholine, an adenosine nucleotide, arachidonic acid, bradykinin, cyanide, endothelin, endotoxin, interleukin-2, ionophore A23187, nitroprusside, a leukotriene, an oxygen radical, phospholipade, platelet activating factor, protamine, serotonin, tumor necrosis factor, vascular endothelial growth factor, a venom, and a vasoactive amine See, e.g., WO 99/31982, Jul. 1, 1999. Alternatively, other methods for targeted delivery to the heart may be utilized.

In addition, the methods of the invention may be used in combination with conventional delivery of other active ingredients or other methods. For example, it may be desirable to perform the method of the invention in a regimen that involves sequential delivery of a desired heterologous molecule to the cardiac muscle by targeted delivery to the heart. See, e.g., WO 99/59666.

In another embodiment, the invention provides a method described for targeted delivery to the heart muscle. Notably, in an experimental series, the inventors showed that retrograde perfusions of the heart via the coronary veins, followed by heterotopic transplantation can be successfully utilized to eliminate the need for the use of an inflammatory mediator or vasodilator to achieve highly efficient gene transfer. Implementation of this in the heart in situ requires separation of the coronary and systemic circulations, using in a preferred embodiment a modification of the system previously detailed [Bridges, et al, Annals of Thoracic Surgery, 73:1939-1946 (2002), incorporated by reference] coupled to retrograde infusion. In the present context, the coronary and systemic circulation are as described in Bridges, et al et al. and this aspect of the invention involves isolating the cardiac circulation from the remainder of the patient's circulatory system. In this embodiment, the heart is cooled to about 15 to 18° C., but the patient is not required to undergo complete exsanguination. Nor is the remainder of the patient subjected to hypothermic conditions. Suitably, the systemic circulation of the patient is provided with constant, high level, oxygenated fluid using techniques known for use in cardiopulmonary procedures.

Figure 7:
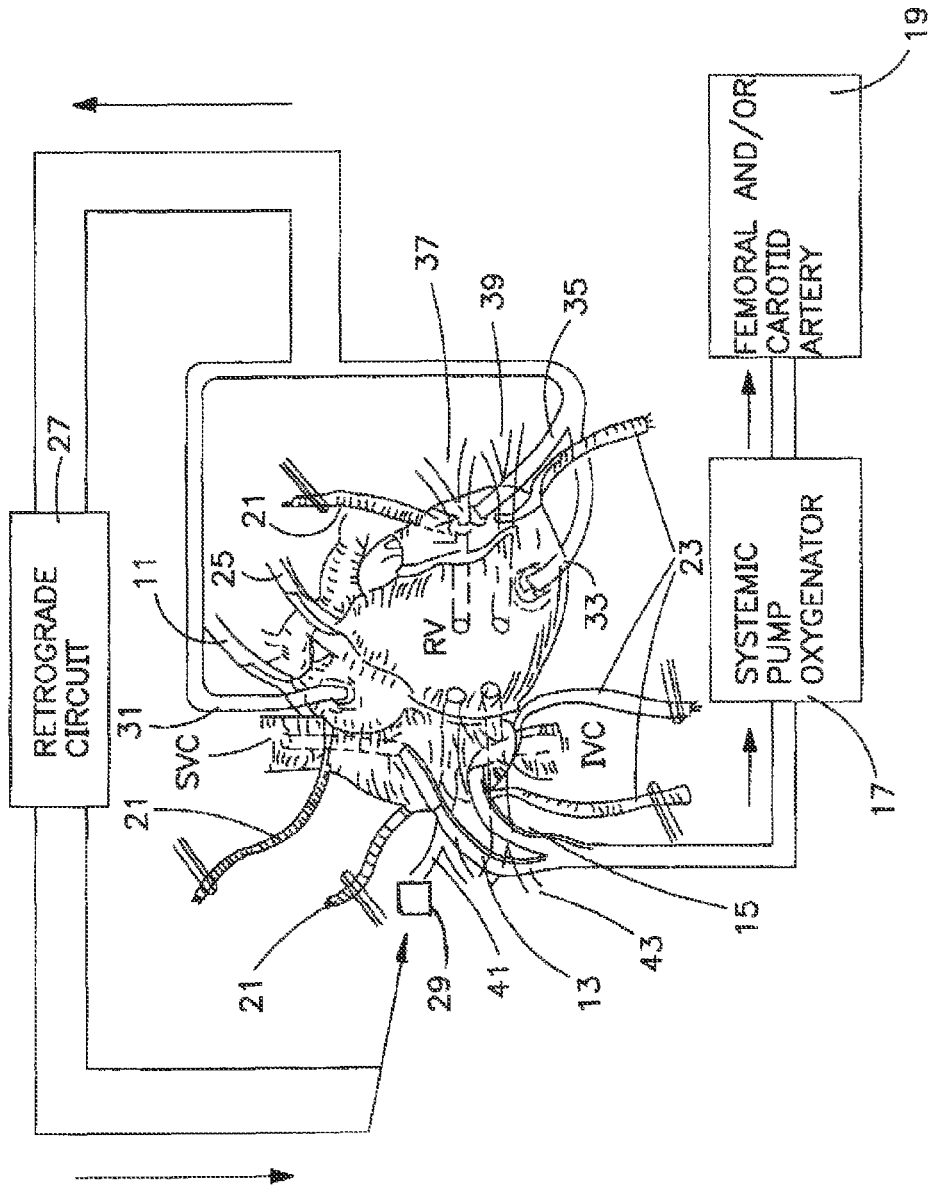
FIG. 7 illustrates an open chest during a cardiopulmonary procedure. Illustrated are all important components of the cardiac isolation method of the invention, including the aortic cross-clamp 11, superior vena cava (SVC) cannula 13 and inferior vena cava (IVC) cannula 15, SVC 21 and IVC 23 snares, pulmonary cross-clamp 25, cardiac arterial in-flow 31, right ventricular (RV) 33 and left ventricular (LV) vent catheters 35, and the coronary sinus catheter 29.

See, FIG. 7, which illustrates the important components of the cardiac isolation method of the invention, including the aortic cross-clamp 11, superior vena cava (SVC) and inferior vena cava (IVC) cannulae 13 and 15, respectively, which are connected to a systemic pump oxygenator 17, which returns blood to the patient's femoral and/or carotid arteries through a cannula 19. The components also include SVC 21 and IVC 23 snares and a pulmonary cross-clamp 25. Retrograde perfusion takes place in a recirculating pathway 27, through a coronary sinus catheter 29 and through a cardiac arterial in-flow catheter 21, a right ventricular (RV) catheter 33 and a left ventricular (LV) vent catheter 35, which have been described in Bridges, et al., The present invention further utilizes a coronary sinus catheter 29 that is inserted into the right atrium and into the coronary sinus to achieve retrograde perfusion. The left pulmonary veins 37 and 39 and right pulmonary veins 41 and 43 are depicted for perspective. Using these techniques, the cardiac circulation is infused with a heterologous molecule such as has been described herein and the use of retrograde perfusion permits high levels of transfer into the venous interstitium, thereby enhancing transfer into the cardiac muscle as compared to methods known in the art and avoiding transfer of the heterologous molecule to the remainder of the patient.

IV. Balloon Catheter

In one embodiment of an internal occlusion balloon catheter in accordance with the invention, the balloon extends from a point adjacent the distal end of the cannula (i.e., the end which first enters the patient through a cannulation site) to a point adjacent the proximal end of the cannula. This balloon catheter differs from conventional balloon catheters, in which the balloon is typically situated at the distal end of the cannula, and also from other balloon catheters, in which the balloon is situated at or near the proximal end or in which balloons are situated at both the distal and proximal ends, with a significant separation between them. The balloon in accordance with the invention may take the form of a single, elongated, tubular envelope having a continuous internal space for expansion fluid, or alternatively, an elongated envelope having plural internal compartments or segments, isolated from one another by radial membranes which connect the outer part of the balloon envelope to the cannula, thereby anchoring the balloon envelope against axial translation along the length of the cannula. In each case, the balloon envelope, when inflated, that is, when expanded by a suitable expansion fluid, is an elongated, substantially continuous, cylindrical tube having rounded ends, and extends from a location adjacent the distal end of the cannula, toward the proximal end throughout an appropriate distance such that the balloon, when inflated can substantially fill the blood vessel into which it is inserted throughout the entire length of the vessel.

When the balloons of the catheters are inflated within the aorta or vena cavae, they initially encounter relatively little resistance as the walls of the vessels expand. However, when the vessel reaches their fully expanded condition, the collagen component resists further expansion, and the vessel walls then exert a counterpressure on the balloons. In general, the balloons should be made of a material having a very high degree of distensibility so that they can exert pressure on all parts of the walls of the vessels in which they are situated, expanding the vessels to the point at which further expansion is resisted by the collagen in the vessel walls, and thereby fully occluding the vessels. However, as explained below, in the case of a balloon catheter for insertion into the vena cavae, the portion of the balloon that is ultimately situated in the right atrium of the heart is sufficiently limited in its distensibility to avoid overdistension of, and resultant damage to, the heart. In one embodiment, a venting catheter is placed in the right atrium to relieve pressure.

In this embodiment, the balloon catheters extend substantially the full length of the vessels in which they are situated in order to facilitate compartmentalization of the circulation in the central and peripheral vascular systems. The central vascular system comprises named vessels directly supplying the thoracic and abdominal viscera, and the peripheral vascular system comprises named vessels supplying the skeletal muscle mass. When, in the process of delivering the macromolecular complex, high venous pressure is applied to the peripheral circulation, the pressure within the balloon catheters transiently restricts flow from the peripheral to the central circulation. Transient separation of the central and peripheral circulation promotes efficient vector delivery to the skeletal muscle interstitium, while the heart is protected from overdistension. In addition, vector transport to the abdominal viscera is minimized by the restriction of flow through the aorta and vena cavae, as they interconnect the named vessels supplying the thoracic and abdominal viscera.

Those skilled in the art can select from among various known materials, shapes and designs for the catheter. The catheter comprises an elongated shaft which will ordinarily be hollow so that it serves as a cannula. The cannula is preferably formed of a flexible thermoplastic material, a thermoplastic elastomer or a thermoset elastomer. The cannula may be fabricated from components separately extruded and joined together end-to-end, for example by heat welding or by adhesive bonding. The cannula may also be fabricated by dipping, or by composite construction techniques, in which separately fabricated components are joined together. Alternatively, the entire cannula may be fabricated as a unit. Suitable materials for the elongated catheter shaft include, but are not limited to, polyvinylchloride (PVC) polyurethane, polyethylene, polypropylene, polyamides (nylons), polyesters, silicone, latex, and alloys or copolymers thereof, as well as braided, coiled or counterwound wire or filament-reinforced composites.

Of course, many other general catheter designs are known to those of skill in the art, and can find useful application within the context of the invention. See, e.g., WO 99/59666, Nov. 25, 1999.

FIG. 1 depicts an embodiment of the balloon catheter 101, designed for insertion into the aorta. In order to facilitate placement of the catheter and to improve the stability of the catheter and thereby maintain it in the proper position in the patient's aorta, a distal region 102 of the cannula is preshaped in a curve to match the internal curvature of the patient's aortic arch. The catheter is J-shaped, with its distal region formed in an arcuate curve subtending an angle of approximately 180 degrees. In the case of an adult human patient, the arcuate curve should have a radius of curvature of approximately 2 to 4 cm, to match the typical curvature of the adult aortic arch. The distal end of the cannula may be skewed slightly out of the plane of the curve to accommodate the angle of the patient's ascending aorta. Additionally, the cannula (catheter shaft) may be reinforced, particularly in the curved distal region, for example by braided or coiled wire, to improve the stability of the catheter still further, and thereby ensure that it can be maintained in the proper position in the patient's aorta.

As shown in FIG. 1, an inflatable balloon 103 surrounds the cannula, and is secured to the cannula at a point adjacent the distal end of the cannula (i.e., the end which first enters the patient through the cannulation site), and also at a point spaced by a suitable distance from the distal end. In some cases, the balloon extends to a location adjacent the proximal end of the cannula. However, in other cases, as depicted in FIG. 1, a portion of the cannula will extend proximally relative to the proximal end of the balloon so that an externally extending part of the catheter is provided for manipulation. Also, in some applications in accordance with the invention, it may be desirable to have the balloon extend only along a portion of the blood vessel spaced from the catheter entry point. For example, in the case of a balloon catheter intended for occlusion of the aorta, the balloon, may be located only above the bifurcation where the abdominal aorta branches into the iliac arteries, and therefore spaced by a considerable distance from the catheter entry point in a femoral artery.

The balloon may be secured to the cannula by any of various known fastening schemes such as adhesive bonding, heat welding, wrapping with a winding of filamentary material, or combinations of adhesive bonding or heat welding and reinforcing material, or the like. In the case of a balloon having a single, uninterrupted, internal space, the balloon will ordinarily be secured only at its distal and proximal ends to the catheter. However, radial connections in the form of membranes or filaments may be provided between the cannula and the balloon at intermediate locations. Alternatively, as will be described below, the balloon may comprise a series of separate balloon-like segments disposed along the shaft in end-to-end relationship to form a balloon that is essentially a single balloon when viewed from its exterior, but which is composed of plural compartments isolated from one another by membranes formed by the ends of the balloons where they meet each other. In all of the cases in which the balloon is attached to the cannula at intermediate points as well as at the ends of the balloon, the multiple attachment sites assist in avoiding longitudinal movement of the inflated balloon, which may be caused by inflation and/or backflow.

The cannula contains an interior lumen for conducting an expansion fluid to the interior of the balloon. A conventional balloon catheter is provided with fluid conducting apertures located at its distal end for conducting expansion fluid from the interior lumen to the exterior of the cannula for inflation of the balloon. However, because the length of the balloon of the invention is much longer than that of conventional balloons, the cannula may have multiple apertures located along its length. Optionally, a series of such apertures may be placed in proximity to one another and spaced apart from another series of apertures. Typically, a series of apertures is composed of two or three apertures that are spaced apart by 3 to 10 mm. In one embodiment, the apertures are disposed in longitudinally spaced relationship along the length of the cannula. Alternatively, a series of apertures may be located at a single station along the length of the cannula, being disposed around the circumference thereof Longitudinally spaced groups of apertures are used in embodiments incorporating a compartmentalized balloon to provide for simultaneous or sequential inflation of the compartments, as described below.

The cannula may have multiple lumens. In addition to at least one lumen for carrying a suitable expansion fluid for inflation of the balloon 103, the shaft may also have a corporeal perfusion lumen, an arch perfusion lumen, an oxygenation lumen, a guide wire and cardioplegia lumen, and a root pressure lumen.

In the embodiment illustrated in FIG. 1, the catheter is provided with a common balloon inflation lumen which extends through the shaft from the proximal end to proximal balloon inflation apertures 105, and continues to distal balloon inflation apertures 107, the proximal and distal inflation apertures being disposed within the balloon, respectively near the proximal and distal ends of the balloon.

Alternatively, separate balloon inflation lumens may be provided, which extend through the cannula shaft from the proximal end to different groups of balloon inflation apertures. The separate balloon inflation lumens permit greater flexibility and precision in inflation of the balloon, or sequential inflation of compartments or regions in the case of a segmented balloon.

Optionally, the catheter can be provided with one or more markers, which may include radiopaque markers and/or sonoreflective markers, to enhance imaging of the catheter by fluoroscopy or ultrasound used to monitor the position and placement of the catheter. Typically, these markers are placed along the distal end of the catheter. Suitable materials for such markers are well known to those skilled in the art, and include, for example, a ring of dense radioopaque metal, such as gold, platinum, tantalum, tungsten or alloys thereof, or a ring of a polymer or adhesive material heavily loaded with a radiopaque filler material.

In the embodiment illustrated in FIG. 2, the balloon 111 is composed of a series of balloon segments, including segments 113-123, each segment being a complete balloon in itself These segments are disposed along the cannula 125 in end-to-end relationship, their ends meeting one another and forming double-walled radial membranes shown, for example at 127 and 129. The membranes isolate the interiors of the balloon segments from one another, and reinforce the balloon structure, resisting longitudinal movement of the balloon along the length of the catheter. Groups of apertures in the cannula 125 are disposed to deliver expansion fluid to the interiors of the individual balloon parts. For example, aperture groups 131 and 133 are positioned to deliver expansion fluid to balloons 113 and 115, respectively. Optionally, the groups of apertures may be in communication with separate inflation lumens within the catheter shaft, thereby allowing controlled inflation of the segments of the balloon. For example, the segments may be inflated sequentially, segment 113 at the distal end of the balloon being inflated first, followed by inflation of segment 115 and then part 117, and so on, until inflation of the balloon segment 123 at the proximal end is achieved. Alternatively, it may be desirable to inflate the segments at the distal and proximal ends, following by inflation of the segments in the regions between the two ends. The balloon may, of course be composed of any desired number of such segments, and the segments may be inflated simultaneously through a single inflation lumen, or separately through different inflation lumens.

In the collapsed state, the balloon fits and conforms to the cannula, so that the diameter of the cannula/balloon combination, when inserted, is only greater than that of the cannula by twice the relaxed balloon wall thickness. In its inflated state, the balloon expands to a diameter sufficient to occlude blood flow in the vessel into which it is inserted. Preferably, the balloon has an inflated length that does not change significantly as compared to its noninflated length. This is especially significant in the case of the aortic arch, where longitudinal expansion could cause damage.

In the case of a balloon catheter intended for use in the aorta, the balloon may extend substantially the entire length of the aorta, as shown in FIG. 3, including the aortic arch. Thus, as shown in FIG. 3, where the catheter shaft 135 is inserted through a femoral artery, the balloon 138 extends from a location adjacent the bottom of the abdominal aorta, through the aortic arch, and into the ascending aorta, thereby substantially filling the entire aorta. As will be apparent from FIG. 3, the occlusion of the entire aorta, effectively prevents cross flow, through the aorta, between the various branch vessels, including the branches leading from the aortic arch, the intercostal arteries, and the lumbar and celiac arteries as well as the superior and inferior mesenteric arteries.

In the case of the vena cavae, as shown in FIG. 4, the balloon catheter preferably comprises a cannula 140, with a balloon consisting of plural, separately inflatable segments in end-to-end relationship, in an arrangement similar to that shown in FIG. 2. In the case of FIG. 4, the balloon comprises three balloon segments 142, 144, and 146. The catheter is preferably inserted through the right jugular vein, and extends through the superior vena cava, and through the right atrium of the heart, to the lower end of the inferior vena cava.

The proximal balloon segment 142 and the distal balloon segment 146 are composed of a highly distensible polymeric material, as in the case of the aortic balloon catheters of FIGS. 1-3. The intermediate balloon segment 144, on the other hand, should have more limited expansibility in order to prevent overdistension of right atrium. Overdistension can cause unraveling the titin in the wall of the right atrium, resulting in a dysfunction of the heart when restarted at the conclusion of the macromolecular transfer procedure. This dysfunction can seriously impede patient recovery.

Overdistension can be avoided by various measures, including selection of a less distensible balloon material for the balloon segment 144, constructing balloon segment 144 with a distension-limiting layer or wrapping, or by inflating balloon segment 144 through a separate inflation lumen, and limiting the amount of expansion fluid introduced into it.

Figure 5:
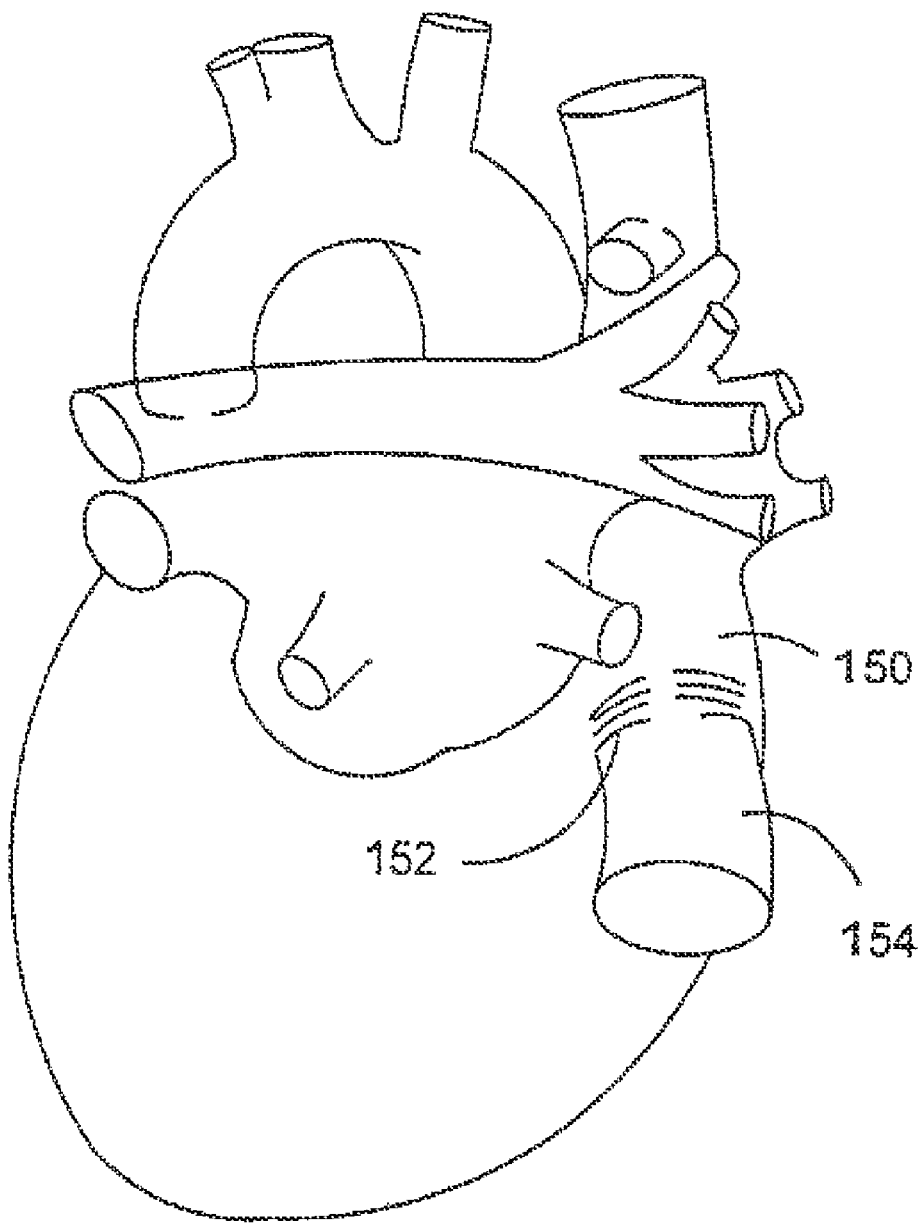
FIG. 5 is a schematic posterior view of the heart of the patient in FIG. 4.

As shown in FIG. 5, the main portion of the inferior vena cava 148 is composed of smooth muscle, but the portion 150 of the inferior vena cava that extends above the boundary 152 where the vessel enters the right atrium of the heart is composed of striated muscle.

Figure 6:
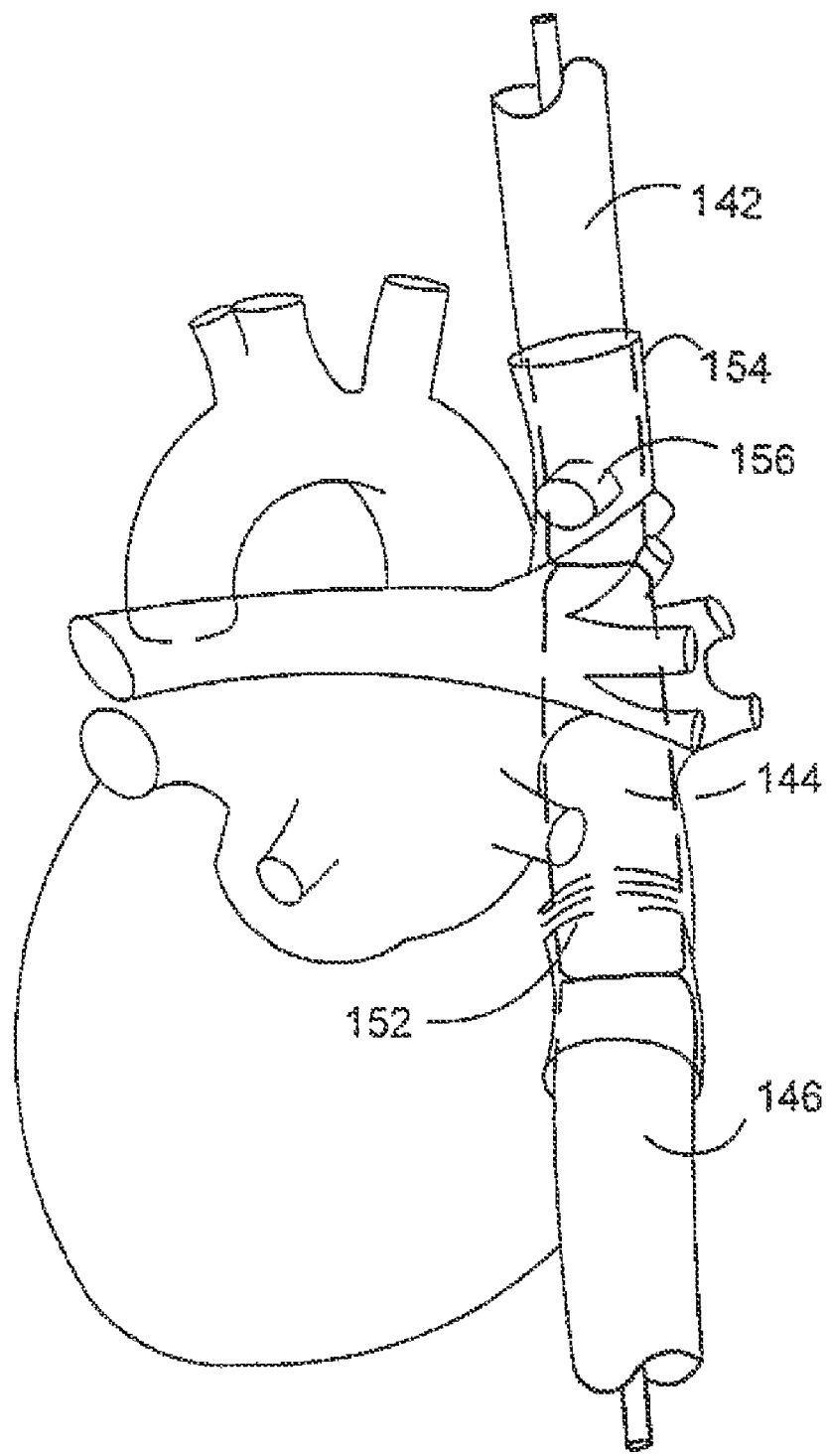
FIG. 6 is a schematic view, similar to FIG. 5, showing details of the balloon catheter placement.

As shown in FIG. 6, balloon segment or compartments 144 should be sufficiently long that, when the balloon catheter is in place in the vena cavae, its lower end extends slightly below the boundary 152, and its upper end extends into the superior vena cava 154, but not to the location where the azygous vein 156 enters the superior vena cava. Consequently, the superior vena cava is occluded by balloon segment 142 at the location of its junction with the azygous vein, but neither of the highly distensible balloon segments 142 and 146 extends into the right atrium. Therefore excessive distension of the right atrium is avoided. Balloon segment 144 prevents segments, or compartments, 142 and 146 from expanding longitudinally into the right atrium, and occludes short portions of the vena cavae immediately adjacent the heart. The balloon segments 142 and 146 prevent cross flow between the various branches of the superior and inferior vena cavae, for example, the azygous vein and the hepatic and renal veins, and also prevent coaxial flow of fluid from the vena cavae into the right atrium.

As shown in FIG. 4, a vent catheter 158, threaded through the internal jugular vein, passes alongside the balloon segment 142 and the upper part of balloon segment 144, into the right atrium. The vent catheter continues, through the tricuspid valve, into the right ventricle. A series of apertures is provided along the distal portion of the vent catheter 158 so that some of the apertures are within the right atrium, and others are in the right ventricle, when the vent catheter is in place. Thus, the vent catheter assists in preventing cardiac distension. Although the vent catheter is shown in FIG. 4 is a separate catheter, the vent catheter can be incorporated into the balloon catheter.

In the case of a catheter intended for use in the aorta of an adult patient, the inflated outer diameter of the balloon will generally be in the range from 1.5 to 5.0 cm and the length of the balloon will generally be in the range from 40 to 70 cm, and preferably in the range from 50 to 60 cm.

In the case of a catheter intended for use in the aorta of a pediatric patient, the inflated outer diameter of the balloon will generally be in the range from 0.5 to 2 cm, and the length of the balloon will generally be in the range from 20 to 30 cm.

In the case of a catheter intended for use in the aorta of an infant, the inflated outer diameter of the balloon will generally be in the range from 0.3 to 1 cm, and the length of the balloon will generally be in the range from 10 to 20 cm.

In the case of a catheter intended for use in the vena cavae of an adult patient, the inflated outer diameter of the balloon will generally be in the range from 2 to 5 cm, and the length of the balloon will generally be in the range from 40 to 70 cm.

In the case of a catheter intended for use in the vena cavae of a pediatric patient, the inflated outer diameter of the balloon will generally be in the range from 1 to 2 cm, and the length of the balloon will generally be in the range from 20 to 30 cm.

In the case of a catheter intended for use in the inferior vena cava of an infant, the inflated outer diameter of the balloon will generally be in the range from 0.3 to 1 cm, and the length of the balloon will generally be in the range from 10 to 20 cm.

Suitable materials for the balloon include materials that exhibit substantially identical expansion properties under the hypothermic conditions described herein (about 15 to 18° C.) as at body temperature (about 37° C.). Examples of suitable materials include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. If the balloon is secured to the catheter shaft by adhesive bonding, the adhesive may be any material compatible with the balloon and catheter shaft materials, and may be composed, for example, of flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the balloon may include a friction increasing coating or texture to increase friction with the aortic wall when deployed.

V. Clinical Kit

In one aspect, the invention provides a kit for use by a clinician or other personnel. Typically, such a kit will contain a balloon catheter of the invention and, optionally, instructions for performing a method as described herein. In another embodiment, the kit will contain a macromolecular complex in a physiologically compatible saline solution and, optionally, instructions for dilution, and performing a method as described herein.

The kit of the invention may also contain an oxygen-transporting agent and/or at least one disposable element of an extracorporeal circulatory support and oxygenation system. For example, at least one disposable element can be an oxygenator having a hollow body, a liquid inlet in fluid communication with the interior of the body, a liquid outlet in fluid communication with the interior of the body, a gas inlet for providing gas to the interior of a gas chamber, at least one gas-permeable membrane separating the gas chamber from the interior of the body, and a gas outlet for permitting gas to exit from the gas chamber, whereby gas exchange is enabled between a fluid in the interior of the body and a gas in the gas chamber. The oxygenator may be constructed as described in U.S. Pat. No. 6,177,403, wherein the gas-permeable membrane comprises PTFE tubing extending within at least a portion of the tube, and wherein the gas chamber comprises the interior of the PTFE tubing.

Thus, the kit of the invention may also comprise an oxygen-transporting agent or at least one disposable element of an extracorporeal circulatory support and/or oxygenation system.

A kit that is useful for performing the method of the invention is contemplated which comprises, in addition to the macromolecular complex and/or balloon catheter of the invention, at least one disposable element of an extracorporeal circulatory support and oxygenation system. Preferably, such a kit comprises all of the single-use components needed to perform the method of the invention, including a macromolecular complex, a vascular permeability-enhancing agent, a fluid delivery instrument such as a syringe or a length of peristaltic pump tubing, and a cannula such as a hollow bore needle adapted to fit a syringe. Such a kit may also contain a pharmaceutically acceptable carrier, a second cannula, an oxygen-transporting agent, a clearance solution which is substantially free of the macromolecular complex, one or more blood vessel occluding devices, such as a clamp, hemostat, or tourniquet, a disposable oxygenator, and the like.

In another embodiment, a method of administering a macromolecular complex to a subject having circulating antibodies to said macromolecular complex is provided, comprising the steps of isolating a region of the subject's microvasculature and exsanguinating the region; and contacting, under high hydrostatic pressure, a subject's microvasculature with a solution comprising a macromolecular complex for delivery to the subject and saline. The method may further comprise the steps of flushing out residual macromolecular complex and resanguinating the patient.

In yet another embodiment, a method of administering a macromolecular complex to the interstitial space of a subject without activating destructive clotting factors or inflammatory response is provided, comprising the steps of isolating a region of the subject's microvasculature exsanguinating the region; and contacting, under high hydrostatic pressure, a subject's microvasculature with a solution comprising a macromolecular complex for delivery to the subject and saline.

In still a further embodiment, a method of transferring a macromolecular complex to a limb of a subject is provided, comprising the steps of (a) placing a proximal inflatable tourniquet or balloon catheter for isolating the vasculature of a limb of a subject; (b) exsanguinating the limb; (c) applying pressure sufficient to isolate the limb at a girdle between the limb and the trunk of the subject's body; and (d) infusing the macromolecular complex into the limb at a high hydrostatic pressure. The macromolecular complex may infused in oxygenated, physiologic saline for a total volume in the range of 20 to 100% of the estimated volume of the extremity.

In another embodiment, an internal occlusion balloon catheter for occluding blood flow through an aorta of a hypothermic patient is provided, comprising a flexible, elongate cannula having a distal end and a proximal end and extending along an axis having an internal channel for the controlled application of fluid under pressure; and an inflatable and radially expandable balloon envelope attached to said cannula and extending from adjacent said distal end of said cannula to adjacent said proximal end of said cannula; wherein in an inflated condition, said balloon envelope forming an elongate, continuous, substantially-cylindrical tube along its full length, and when positioned within the patient's aorta, said full length of said tube of said balloon envelope being of sufficient length to extend continuously from a location adjacent a bottom of the patient's abdominal aorta through the patient's aortic arch and into the patient's ascending aorta thereby substantially filling and occluding flow within the patient's entire aorta and preventing cross-flow through the aorta between various branch vessels branching from the aorta. The cannula and the balloon envelope may be flexible and pre-shaped into a J-shape. The cannula may also have a distal region for location within the patient's aortic arch that is pre-shaped in a curve to match an internal curvature of the patient's aortic arch. The curve of the distal region of the cannula may be an arcuate curve subtending an angle of approximately 180°. The arcuate curve may have a radius of curvature of about 2 to 4 cm, the length of the balloon envelope may be about 40 to 70 cm, 20 to 30 cm, or 10 to 20 cm and the tube may have an outer diameter of about 1.5 to 5.0 cm, 0.5 to 2.0 cm, or 0.3 to 1.0 cm. The catheter may also have multiple lumens including at least one serving as a vent during vector recirculation with a tip of said vent lumen open to a vessel lumen. The balloon envelope may be a single, continuous balloon having an uninterrupted internal space for expansion fluid. The balloon envelope may also include a series of separate balloon segments disposed in end-to-end relationship with no gaps therebetween.

In yet another embodiment, an internal occlusion balloon catheter for occluding blood flow through the vena cavae of a hypothermic patient is provided, comprising a flexible, elongate cannula having a distal end and a proximal end and extending along an axis having an internal channel for the controlled application of fluid under pressure; and a series of inflatable and radially expandable balloons attached to said cannula; wherein in an inflated condition, each of the series of balloons forms an elongate, continuous, substantially-cylindrical tube along its full length, and when positioned within the patient's vena cavae, one of the balloons is of sufficient length to extend continuously from a location adjacent a lower end of the patient's inferior vena cava to just below the right atrium of the patient's heart and another one of the balloons is of sufficient length to extend through the patient's superior vena cava and occlude the azygous vein but does not extend into the right atrium. In a further embodiment, the series of balloons includes an intermediate balloon, wherein the intermediate balloon has a distensibility substantially lower than a distensibility of other of said balloons such that, when the balloon catheter is disposed in the vena cavae of the patient, the intermediate balloon extends within the right atrium of the patient's heart and expansion of the intermediate balloon is prevented from excessively distending the patient's heart. The catheter may also have multiple lumens including at least one serving as a vent during vector recirculation with said vent lumen being open to the right atrium. The length of the tube formed by the series of balloons may be about 40 to 70 cm, 20 to 30 cm, or 10 to 20 cm, and the tube may have an outer diameter of about 2 to 5 cm, 1 to 2 cm, or 0.3 to 1 cm.

EXAMPLES

Selection of appropriate models for these experiments by the inventors reflected the comparative anatomy and morphology of the vascular tree in rodents, carnivores and primates. The seemingly unique absence of valves in the peripheral veins of mice prompted the exclusion of this species from these studies on the grounds that the small size might have facilitated evolutionary loss of the peripheral venous pump mechanism. An additional consideration that prompted the complementary use of one small and one large animal model is the previously documented increase in the thickness of the microvascular basal lamina as a function of postural hydrostatic pressure. Catheters of the largest bore possible for insertion into the distal saphenous veins of the rat and dog, peripheral to and upstream of the valves consistently observed in the larger veins of the proximal limb, were designed. To facilitate pressurized infusion without leak at the venipuncture sites, snug ligatures were placed around the catheters and the veins were ligated distally. Studies using fluorescently labeled albumin suggested that rapid infusion against a proximal tourniquet would force homogenous fluid and solute extravasation throughout the limb, creating a volume of tissue edema several times greater than that of the blood volume in the extremity. To address the size-dependency of the forced extravasation process, recombinant vectors derived from adenoviruses and adeno-associated viruses were substituted. The marker gene LacZ was used to facilitate quantitation and visualization of tissue transduction.

Thus, the following examples are illustrative of the present invention, and describe results for several exemplary macromolecular complexes, including two types of viral vectors and a large, charged proteinaceous molecule (albumin).

The invention is not limited to the methods or apparatus described in these examples.

Example 1

Evans Blue Dye (EBD) Study

EBD solution was prepared as described in C. R. Bridges, et al, Ann Thorac Surg, 73 (6):1939-1946 (June 2002). A male adult Fisher rat underwent hindlimb isolation as described below.

Approximately 0.05 mg/g body weight of EBD was delivered in a sterile PBS & albumin solution. 0.16 ml of the solution was diluted to a volume of 5 ml and infused through the greater saphenous vein with a 400 torr applied pressure into the isolated hindlimb. 2.4 ml of the solution was infused slowly into the contralateral hindlimb without isolation. The rat was necropsied 30 minutes after the start of infusion.

Example 2

Materials

The following materials were used in the studies described in Examples 3 and 4, which demonstrate the method in a rat and canine model, respectively.

A. rAAV and rAd

All vector was procured through University of Pennsylvania Vector Core and was tested to be replication defective and endotoxin negative.

All vector used encoded the marker gene lac-Z coupled to a CMV promoter. Varying lots of vector were used for experiments with the goal of delivering ~$10^{13}$ genome copies (GC)/kg of rAAV and $10^{12}$ particles/kg of rAd5 in isolated limb infusion studies. The isolated hemibody trials delivered ~$5 \times 10^{13}$ GC/kg of rAAV. rAAV serotype 2/1 was utilized for all experiments except for preliminary studies in the rat using rAAV serotype 2/2. The rAAV 2/1 used in the dogs was an aggregate pool of 5 lots.

B. Tissue Analysis

Tissue samples were 'snap frozen' in isopentane cooled in liquid nitrogen at the time of necropsy. 8 micron sections were generated using a cryotome and then incubated overnight at 37° C. in PBS supplemented with 5-bromo-4-chloro-3-indolyl β-D-galactopyranoside (X-gal; Sigma), magnesium chloride, and Fe(II,III)CN (potassium ferro/ferricyanide). After completion of reaction incubation, the tissues were counter-stained with hematoxylin and eosin, no bluing agent was used. Tissue specimens from rats were whole-mount-stained for lacZ activity after fixation with 0.2% glutaraldehyde and 2% paraformaldehyde in PBS at necropsy. Protein extracts from the tissues of treated animals were assayed for β-gal activity using a luminometric kit (Applied Biosystems, Foster City, Calif.) and measured for protein concentration with the Bradford reagent (Pierce).

Example 3

Gene Transfer in Rat Model

A. Intravascular Injection of rAAV in Rat Isolated Limbs

After anesthesia with xylene and ketamine, inbred (male adult Fisher 344) rats underwent femoral artery and vein isolation with transmuscular placement of two overlapping 2-0 prolene tourniquets at the level of the proximal thigh. Through a small incision, the greater saphenous vein was cannulated with heat-tapered polyethylene tubes (PE 10; Becton Dickinson, Sparks, Md.) attached at their other ends to 30-gauge needles was performed. After tourniquets were tightened and the limb circulation was isolated, a total volume of 5 ml of sterile PBS and $10^{12}$ GC of rAAV encoding the lac-z marker gene was infused at pressures of 100, 200, 400 torr. The infusion time varied with delivery pressure, but the total time the rAAV solution was left in place was 30 minutes from the beginning of infusion. The tourniquets were then released and the catheter removed. The saphenous vein was ligated with a silk suture and the incision was closed with resorbable suture. The same procedure was followed without tourniquet placement to approximate zero torr pressure infusions. Realizing the volume and rate of infusion may have an impact on intravascular pressure, we performed slow continuous infusions of 5 ml and 0.5 ml with the same quantity of rAAV, $10^{12}$ GC. A simple intramuscular (i.m.) injection of rAAV was delivered to the tibialis anterior muscle on the contralateral limb as a positive control.

The results with at least two animals in each group showed that both AAV 2 and AAV 1 vectors efficiently transduced muscle fibers throughout the limb and that the higher the pressure used the greater the efficiency of transduction.

B. Assessment of Adenovirus (Ad Vector) and Intravascular Injection of rAAV in Rat Lower Hemibody The protocol described in Part A was subsequently modified in three ways: 1) substitution of recombinant adenovirus vector for AAV, 2) simultaneous infusion of AAV vector at 200 torr into one hindlimb and one forelimb with proximal tourniquets at both limb girdles, and 3) simultaneous infusion of AAV vector at 200 torr into both hindlimbs against an extracorporeal tourniquet placed at the mid-abdomen. For 3), adult Fisher 344 male rats underwent lower hemi-body delivery of the transgene after cannulation of both hindlimb saphenous veins. Twice the genomic copies of the vector was diluted in 10 ml of sterile PBS and delivered at 200 torr after atraumatic tourniquet placement at the level of the infraumbilical abdomen. Necropsy was performed at day 14.

All three of these modifications were well tolerated by the rats, as judged by their rapid and complete recovery of normal patterns of activity including normal voluntary movement of all four extremities. Findings at completion of the experiments (7 days for #1, 4 weeks for #2 and 3), were notable for high-level marker gene expression indicative of efficient vector transduction among the majority of muscle fibers throughout the muscles below the level of the tourniquets in each experiment.

Both the pattern of tissue transduction and the total amount of transgene product detected depended entirely on the method of infusion used. Simple low pressure infusion of vector into a peripheral vein resulted in control (i.e., indistinguishable from that in uninjected animals) levels of muscle transduction throughout the body. In contrast, moderate (100 torr) and high pressure (400 torr) infusion of the same total dose of vector, in conjunction with tourniquet occlusion at a proximal site, resulted in uniform transduction of muscle fibers at an efficiency approaching 100%. Histochemical assays for Xgal activity revealed levels an average 1000-fold higher than background in the latter groups, while there was no detectable difference from background in the rats receiving simple intravenous infusions of vector. Rats infused at lower pressure (50 torr) below a tourniquet had low but still detectable levels of transduction in an inhomogeneous pattern localized primarily near the distal site of infusion. Finally, anesthetized rats in which a tourniquet was placed to encircle the caudal abdomen, (occluding the anatomic homologue to the human infrarenal aorta and inferior vena cava) showed homogenous transduction of muscles surrounding the pelvic girdle (e.g., gluteus). All animals tolerated the procedures well, and gradually mobilized the interstitial fluid loads without signs of cardiopulmonary compromise as they rapidly returned to their pre-procedural weights. Normalized to the titers of input vector, the absolute values of tissue X-gal were similar in animals infused with AAV vectors bearing capsids of serological classes 1 and 2.

Example 4

Canine Animal Model

As proportionally larger quantities of vector became available, similar studies were undertaken in a large animal model. The results were scale-independent in comparisons between the rat and dog.

A. Intravascular Injection of rAd and rAAV in Dog Isolated Limbs

Mixed hound male canines 5-11 weeks in age and weighing 5-11 kg were infused with rAAV ($10^{14}$ GC) and rAd ($10^{13}$ particles) diluted in 500 ml of sterile PBS at a delivery pressure of 300 torr. Following intravenous sedation with medetomidinine hydrochloride (Dormitor® brand, Novartis Animal Health) and butorphenol, dogs underwent greater saphenous vein cannulation through a small incision (~2 cm) with a 20 gauge angiocatheter. An atraumatic tourniquet was placed at the level of the groin, secured in place to prevent distal migration, and tightened until the femoral pulse could no longer be palpated. The infusion was begun with the aid of a pressure bag inflated to the maximum level (300 torr) through standard IV tubing with care to ensure that no air could enter the vein. The total time of infusion with dwell was twenty minutes. The tourniquet was then released and the cannula was removed. The saphenous vein was ligated with a silk suture and the incision was closed with resorbable suture. Necropsies were performed at day 14. The same procedure was performed without tourniquet placement as control.

B. Results

Despite the readily discernable increase in the histological thickness of the canine perimysial and epimysial fascia, the pattern of and extraordinary efficiency of transduction reflects uniform vector distribution and extravasation throughout the entire hindlimb. Similar histochemical results were obtained with adenovirus and AAV. Based on our earlier studies comparing X-gal staining for beta-galactosidase and immunofluorescence staining for disease-specific transgene products, we expected the current approach to meet the gene delivery requirements for therapeutic efficacy in hemophilia and muscular dystrophy. All dogs tolerated this procedure well, generally returning to full, symmetrical weight bearing within minutes of completion of the procedure. Periprocedural monitoring documented no significant alterations in pulse, blood pressure, or arterial oxygen saturation. Of note, these procedures were all performed using mild, rapidly reversible sedation with medetomidinine hydrochloride (Dormitor® brand, Novartis Animal Health) and atipamezde hydrochloride (a medetomidinine reversing agent, Antisedan® brand, Novartis Animal Health), without the need for endotracheal intubation or mechanical ventilation. None of the dogs in this series demonstrated any clinical signs of muscle or cardiovascular dysfunction referable to the procedure.

The experimental findings are consistent with the inventors' theory for mechanical distention and perturbation of the endothelial sheet, and for the pattern of generally afferent but locally retrograde flow through the venous arcade.

In mammals, most of the ultrastructural dimensions of the microvasculature are scale-independent. A notable exception of relevance to translational studies in gene therapy is the thickness or width of the basement membrane, a parameter which increases in proportion to the average transmural distending pressure. In all but the smallest mammals, constraints on regulation of the central venous pressure require thicker basement membranes in the limbs than in the central circulation, perhaps explaining the relative ease with which systemic gene delivery can be obtained in the mouse.

All documents identified herein are incorporated by reference. Numerous modifications to, and variations of, the specific embodiments described herein will be readily apparent to one of skill in the art. The appended claims are intended to be construed to include all such embodiments and equivalent variations.

What is claimed is:

1. A method of systemically transferring a macromolecular complex to muscle cells of a subject, said method comprising the step of:
   placing a patient under total circulatory arrest using a first heart-lung cannulae and a second heart-lung cannula, each said cannula being placed in a suitable vessel through a cannulation site in each vessel;
   lowering the patient's temperature to 15 to 18° C.;
   partially exsanguinating and decannulating the patient from the first and second heart-lung cannulae;
   introducing a first balloon catheter and a second balloon catheter in the cannulation sites, wherein upon inflation the first balloon catheters occludes the aorta and the second balloon catheter occludes the venae cavae to preclude backflow;
   inflating the balloon catheters to a pressure exceeding that applied from cannulae in extremities of the patient; and
   simultaneously applying the macromolecular complex in solution to all four of the patient's extremities via the cannulae located therein;
   wherein each of said first and second balloon catheters comprises:
   an inflatable balloon having an interior, said balloon being expandable radially without significant distal expansion, and, when inflated, said balloon forming an elongate, continuous, cylindrical tube having an outer diameter that is substantially constant along a full length of said tube and that is sufficient to abut the walls of a vessel in which it has been inserted to occlude blow flow therethrough;
   a flexible cannula having a distal end and a proximal end and extending along an axis having an internal channel for the controlled application of fluid under pressure;
   said balloon being attached to the cannula at at least two points, one point of attachment being adjacent to the distal end of the cannula and a second point of attachment being adjacent to the proximal end of the cannula, such that when inflated, said balloon expands radially to abut the walls of the vessel in which it has been inserted and to occlude the aortic space or the venae cavae.

2. The method according to claim 1, wherein the solution is allowed to dwell for a period of about 5 to 30 minutes.

3. The method according to claim 1, further comprising the steps of:
   flushing out residual macromolecular complex;
   withdrawing the balloon catheters;

reinserting the heart-lung cannulae, resanguinating and rewarming the patient.

4. The method according to claim 1, wherein the balloon catheters comprise an inflatable balloon which extends the length of the cannulae such that upon inflation it expands radially to abut the walls of the vessel, the aortic space and the venae cavae.

* * * * *